United States Patent [19]
Gluzman et al.

[11] Patent Number: 6,110,901
[45] Date of Patent: Aug. 29, 2000

[54] METHOD FOR TREATING RNA VIRAL INFECTIONS BY USING RNA CHAIN TERMINATORS

[75] Inventors: Yakov Gluzman, Upper Saddle River; Michael Ostrander, Glenridge, both of N.J.

[73] Assignee: American Cyanamid Company, Madison, N.J.

[21] Appl. No.: 07/839,728

[22] Filed: Feb. 19, 1992

Related U.S. Application Data

[63] Continuation of application No. 07/547,889, Jul. 3, 1990.
[51] Int. Cl.$^7$ .................................................. A61K 31/70
[52] U.S. Cl. ................................................ 514/46; 514/49
[58] Field of Search ........................................ 514/46, 49

[56] References Cited

U.S. PATENT DOCUMENTS

| | | | |
|---|---|---|---|
| 4,665,062 | 5/1987 | Eriksson et al. | 514/120 |
| 4,968,690 | 11/1990 | Morquez et al. | 514/303 |

OTHER PUBLICATIONS

Gosselin, G. et al., Systematic Synthesis and Biological Evaluation of alpha– and beta–D–Xylofuranosyl Nucleosides of the five naturally occurring bases in nucleic acids and related analogue. J. Med. Chem. 1986,29,203–214.

Axelrod, V.D. et al. R.S. Specific termination of RNA polymerase synthesis as a method of RNA and DNA sequencing. Nucleic Acids. Res. 1978,5, 549–3553.

Axelrod, V.D., et al. Transcription from bacteriophage T7 and SP6 RNA polymerase promoters in the prescense of 3'–deoxyribonucleoside 5'–triphosphate chain terminators. Biochemistry, 1985,24,5716–5723.

Goswami, B B. and Sharma, S.K. Inhibition of vaccinia virus growth and virus–specific RNA synthesis by 3'–O–methyl adenosine and 3'–O–methyl guanosine. J. Virology. 1983,45,1164–1167.

Puech, F., Gosselin, G., Imbach, J–L. Synthesis of 9-(3–Deoxy–3–fluor–D–ribofuranosyl)guanine, a new potent antiviral agent. J. Chem. Socl, chem. Commun., 1989,955–957.

Plotch, S. J. Palant, O., and Gluzman Y. Purification and properties of poliovirus RNA polymerase expressed in *Escherichia coli*, J. Virology, 1989, 63,216–225.

Plotch, S. J. and Krug, R.M. Influenze virion transcriptase: Synthesis in vitro of large, polyadenylic acid–containing complementary RNA. J. Virology, 1977,21,24–24.

Plotch, S. J. Tomasz, J.M. and Krug, R.M. Absence of detectable capping and methylating enzymes in influenzae virions. J. Virology, 1978,28,75–83.

Beckes, J.D., Haller, A.A., and Perralut, J. Differential effect of ATP concentration on synthesis of vesicular stomatitus virus leader RNAs and mRNAs. J. Virology, 1987, 61,3470–3478.

Tuschall, M. Hiebert E., et al., Poliovirus RNA–dependent RNA polymerase synthesized full–length copies of poliovirion RNA, cellular mRNA, and several plant virus RNA in vitro. J. Virology. 1982,44,209–216.

Yokota et al CA 113: 184252q 1990.
Morozumi et al CA 111: 154308d 1989.
Webb et al CA 109: 23303v 1988.
Widell et al CA 104: 199470x 1986.
Akherm et al CA: 95533h 1978.
Kraus et al CA 113: 147783 1990.
Schuman et al CA 109: 88675b 1988.
Eriksson et al CA 112: 18103b 1989.

*Primary Examiner*—Russell Travers
*Assistant Examiner*—Larry Buit
*Attorney, Agent, or Firm*—Anne M. Rosenblum; Estelle J. Tsevdos

[57] ABSTRACT

The present invention relates to methods for controlling and/or treating RNA-replicating viral infections which afflict human beings, animals and/or plants. Specifically, the RNA chain terminating agents, 3'-deoxyribouracil, 3'-deoxyriboguanine and 3'-deoxyribocytosine are useful in treating RNA-replicating viral infections.

9 Claims, No Drawings

METHOD FOR TREATING RNA VIRAL INFECTIONS BY USING RNA CHAIN TERMINATORS

This is a continuation of co-pending application Ser. No. 07/547,889 filed on Jul. 3, 1990.

BACKGROUND OF THE INVENTION

The present invention relates to a method for treating RNA viral infections by utilizing the type of specified RNA chain terminating agents disclosed herein. The class of compounds useful in treating those viral infections are 3'-substituted ribonucleosides. In contrast to the extensive literature treatment wherein the effects of 2'-deoxy, 3'-substituted nucleosides were studied, the agents disclosed herein useful in the method of the present invention relate to agents acting as RNA chain terminators, particularly as potent inhibitors of RNA virus replication. Although not wanting to be limited by theory, it is believed that these compounds interfere with messenger RNA synthesis and also block viral genome replication.

In the past, numerous alpha and beta-D-ribofuranosyl nucleosides had been used to study antiviral activity against Herpes simplex virus-1, Herpes simplex virus-2, Vaccinia virus, Vesicular stomatitius virus, Poliovirus-1, Coxsackie virus B4, Parainfluenza virus-3, Reovirus, Sindbis virus, Semliki forest virus, Rhinovirus 1A, Rhinovirus-9. Of the various compounds studied in relation to these viruses, three compounds in particular showed marked biological activity. However, the compounds of the present invention have not been studied specifically for RNA viral activity.

More recently, 3'-O-methyl nucleosides have been shown to inhibit Vaccinia virus RNA synthesis in infected cells and 3'-fluoroguanosine has been shown to be an antiviral agent. The viruses reviewed with the fluoroguanosine are Reovirus 1, Sindbis virus, Coxsackie virus and Semliki forest virus.

An object of the present invention relates to providing a mechanism by which to correlate in vitro RNA chain terminator studies with in vivo such studies leading to the use of RNA chain terminators in controlling and/or treating RNA viral infections. Further, it is an object of the present invention to provide a method for treating RNA viral infections. These and/or other objects of the invention will become clearer with the more detailed description of the invention provided hereinbelow.

SUMMARY OF THE INVENTION

The present invention relates to a method of controlling and/or treating RNA viral infections by utilizing RNA chain terminators. Viral infections resulting from the following types of viruses are prevented and/or controlled by administering the RNA chain terminators disclosed herein as well as other such analogues to an (warm-blooded) animal or plant. The viruses include positive, negative and/or double-strand RNA viruses such as picornaviruses (included but not limited to poliovirus, rhinoviruses, hepatitis A), togaviruses, orthomyxoviridae, Bunyavididae and Arevavirdae), rhabdoviridae and paramyxoviridae which infect animals and human beings, are included. An RNA chain terminating agent is administered to said animal or plant. Further, the present invention relates to the use of specific 3'-substituted ribonucleosides useful in antiviral therapy. More specifically, 3'-deoxyribouracil (d-U), or (d-UTP), 3'-deoxyribocytosine (d-C) or (d-CTP) and 3'-deoxyriboguanine (dG) or (d-GTP) are useful RNA chain terminating agents. Although, 3'-deoxyriboadenine (dA) or (dATP) is also an RNA chain terminating agent, it may have toxicities associated with its use in vivo.

All plants and animals infected by RNA replicating viruses can be treated by the method of the present invention. For instance, in the plant area, viral infections caused by plant Comoviruses are RNA replicating viruses which can be controlled and/or treated by the method of the present invention. More specifically, tymoviruses, sobemoviruses, tombusviruses, tobacco necrosis virus, luteoviruses, tobamovinuses, potexviruses, potyviruses and closteroviruses are monopartite genomic viruses controlled and/or treated by the methods of the present invention. Bipartite genomic RNA-replicating viruses which are included in the present methods are comoviruses, nepoviruses, tobraviruses, dianthoviruses, pea enation mosaic virus and furoviruses. Tripartite genomic RNA-replicating viral infections controlled and/or treated by the methods of the present invention include diseases caused by the following viruses: alfafa mosaic virus, flarviruses, bromoviruses, cucumoviruses, hordeiviruses and tomato spotted wilt virus.

In the animal health and nutrition area, all animals infected by RNA replicating viruses can be treated with the present method. For instance, picornavirus is responsible for avian encephalomyelitis, duck hepatitis and calicivirus (cat) infections. Orthomyxovirus is responsible for fowl plague and avian influenza. Coronavirus causes infectious bronchitis and coronaviral enteritis in poultry and canine corona virus in dogs. Togavirus is responsible for pheasant encephalitis; paramyxovirus causes Newcastle's Disease in poultry and canine distemper and parainfluenza in dogs. Rhabdovirus is responsible for rabies and viral hemorrhagic disease in fish (cold-blooded animal RNA replicating viruses are also included herein). Finally reovirus is responsible for poultry infectious bursal disease.

In the human disease area such diseases as polio, respiratory tract influenza and Hepatitis A and other very serious diseases such as measles, mumps, rabies and vesicular stomatis virus are controlled and/or treated by the present invention. Reovirues include Colorado tick fever.

Drug dosages useful in treating human beings or animals range from 0.01 mg/kg to 10,000 mg/kg. With regard to plants treatment, drug concentrations of 0.001 mM to 100 mM are useful.

DETAILED DESCRIPTION OF THE INVENTION

EXAMPLE 1

In Vitro Viral RNA-Dependent RNA Polymerase Assays

Recombinant poliovirus RNA polymerase is purified from bacterial strain BL21(DE3)LysS harboring plasmid PT7-POL following induction with isopropyl-β-thiogalactopyranodie(9). This bacterial strain was obtained from Dr. W. Studier, Brookhaven National Laboratories, Long Island, N.Y. The enzyme is assayed by determining its poly(A)-dependent oligo(U)-primed poly(U) polymerase activity. Assays are performed at 30° C. for 1 hr in $25\mu$ reaction mixtures containing $1.0\mu$ of purified enzyme, 50 mM herpes buffer PH 8.0, 10–100 $\mu$M UTP, 5 mM DTT, 3.5 mM magnesium acetate, 0.06 mM zinc sulfate, 20 ug rifampin per ml, 1.0 ug of oligo($^U$15-30) 2.5 ug of poly(A), and 2.5 uCI of [$\alpha$-$^{32}$P]UTP. When included, 3'-deoxy UTP is added over a concentration range indicated in the tables hereinbelow. Reactions are stopped with 10 mM EDTA, and the labeled product collected by precipitation on GN-6 membrane filters with ice-cold 10% trichloroacetic acid in the presence of 100 μg carrier RNA. The filter radioactivity is measured by liquid scintillation counter techniques. The enzymes are also assayed for RNA-dependent RNA polymerase activity. Transcription reactions are performed using the conditions described above for transcription of poly(A) homopolymer, except that 400 μM adenosinetriphosphate (ATP), cytosinetriphosphate (CTP), guaninetriphasphate (GTP), 15 uM uraciltriphasphate (UTP), 20 ng oligo(UH15-30), and 12.5 uCI of [α-$^{32}$P]UTP, 0.5 mM ATP, 0.05 mM UTP are used. When included, 3'-deoxynucleoside triphosphate is added at either 0.1 or 0.25 mM final concentration. The concentrations of CTP and GTP vary depending on the 3'-deoxynucleoside triphosphate present in the reaction. When 3'-deoxy-UTP is added, CTP and GTP are present at 0.5 MM. When 3'-deoxy-CTP is added, CTP is present at 0.05 mM and GTP at 0.5 mM. Controls containing the variable amounts of CTP or GTP but without added 3'-deoxynucleoside triphosphates are included in all assays. Reaction aliquots are stopped and the labeled products collected and counted as described above for the poliovirus poly(U) polymerase assay except that the filter radioactivity is measured in the presence of scintillation fluid (Aquasol).

Vesicular stomatitus virus (VSV) is a gift from Dr. Richard Peluso (Mt. Sinai Medical Center). RNA polymerase activity is measured using detergent disrupted virus (12). Assays are performed at 30° C. and aliquots are removed fro analysis after 30 and 60 min. Reaction mixtures (in 100 μl total volume) containing ul of pelleted virus resuspended in saline, 50 MM Tris-acetate-pH 7.8, 8 mM magnesium acetate, 0.3M potassium acetate, 0.2% NP-40, 5 MM DTT, 5–10 uCi [α-$^{32}$P]UTP, 5 MM ATP, 0.05 mM UTP are used. The concentrations of CTP and GTP and the 3'-deoxynucleoside triphosphates vary exactly as described above for the influenza virus assays.

EXAMPLE 2

In Vivio Assays

Mammalian cell lines, MDCK CCL34 and HeLa cells CCL2 (both obtained under those accession numbers from ATCC culture) are plated in 96 well microtiter dishes at a density of 3.5×10$^4$ cells per well and infected with virus at low multiplicity followed by treatment with drug 24 hours after plating of cells; drug concentrations range from 0.025–12.5 mM. MDCK cells are infected with influenza virus (strain A/NWS) and HeLA cells are infected with HRV 14-14VR-284 (obtained from ATCC) (human rhinovirus 14) or CVB$_3$VR30 (coxsackie virus B$_3$ strain Nancy obtained from ATCC); replicate uninfected cell cultures are treated with drug as toxicity control. At 48 hours after infection the extent of virus growth is determined by ELISA in the case of influenza virus or by the MTT (tetrazolium dye) cell viability assay in the cases of HRV 14 and CVB$_3$. The influenza A (A/NWS)VR-129 (ATCC) virus ELISA assay utilizes a primary monoclonal antibody to the virus hemagglutinin protein and a secondary antibody conjugated to B-galactosidase. Cytotoxicity of drugs in uninfected cell cultures is determined by MTT cell viability assay at 48 hours after drug treatment Mice: Female DBA/2 mice in the weight range 10–12 grams are used to assess the antiviral activity of 3'deoxynucleosides against influenza A virus. Mice are lightly anesthetized by inhalation of $CO_2$ and then infected with influenza A virus (strain A/NWS) by instillation of 10 ul of virus suspension into the nostrils. Virus inoculum containing 5×10$^5$ PFU/ml of mouse passaged virus suspended in PBS containing 2% fetal bovine serum is used. The test compounds are dissolved in PBS at various concentrations and administered to animals by intraperitioneal injection of 0.2 ml of drug solution; doses are either 200 or 600 mg/kg.

EXAMPLE 3

In Vitro Acitvity

It is known (13) that in the presence of an oligo(U) primer, any poly(A)-tailed RNA can serve as a template for poliovirus RNA polymerase with an efficiency similar to that of authentic poliovirus RNA to study inhibition with 3'-substituted analogues. Globin RNA, poly-A-tailed 7.5 Kb RNA (obtained from BRL), and poly(A) homopolymer are used as templates for the RNA transcription reaction. Results with six 3'-substituted nucleotides for the two RNA templates and poly(A) are represented in TABLES I, II and III hereinbelow.

TABLE I

| Molar Ratio of 3'deoxy NTP to NTP | % Inhibition | | 3'-deoxy NTP |
|---|---|---|---|
| | With 0.6 Kb Globin RNA | With 7.5 Kb RNA | |
| 1:1 | 8 | 56 | 3'-d ATP |
| 1:1 | 40 | 74 | 3'-d CTP |
| 1:1 | 39 | 72 | 3'-d UTP |
| 1:1 | 37 | 82 | 3'-d GTP |
| 1:1 | 0 | 7 | 3'-ome ATP |
| 1:1 | 3 | 4 | 3'-ome GTP |
| 5:1 | 45 | | 3'-d ATP |
| 5:1 | 73 | | 3'-d CTP |
| 5:1 | 72 | | 3'-d UTP |
| 5:1 | 68 | | 3'-d GTP |
| 5:1 | 25 | | 3'-ome ATP |
| 5:1 | 0 | | 3'-ome GTP |

TABLE II

| With PolyA-homopolymer and OligoU-primer:* | |
|---|---|
| Molar ratio of 3'-dUTP to UTP | % Inhibition |
| 1:50 | 15 |
| 1:25 | 33 |
| 1:5 | 58 |
| 1:1 | 83 |

*The transcription reactions are performed at 100 uM concentration of UTP. Ten fold reduction of concentration of both 3'-dUTP and UTP does not change the % inhibition.

TABLE III

| Detergent-disrupted virus RNA transcription assays: | | |
|---|---|---|
| Molar ratio of 3'-deoxy NTP | % Inhibition | 3'-deoxy-nucleoside triphosphate |
| Influenza virus: | | |
| 2:1 | 10 | 3' deoxy-UTP |
| 5:1 | 34 | |
| 2:1 | 4 | 3'-deoxy-CTP |
| 5:1 | 28 | |
| 2:1 | 55 | 3'-deoxy-GTP |

TABLE III-continued

Detergent-disrupted virus RNA transcription assays:

| Molar ratio of 3'-deoxy NTP | % Inhibition | 3'-deoxy-nucleoside triphosphate |
|---|---|---|
| VSV: | | |
| 2:1 | 0 | 3'-deoxy-UTP |
| 5:1 | 15 | |
| 2:1 | 0 | 3'-deoxy-CTP |
| 5:1 | 0 | |
| 2:1 | 13 | 3'-deoxy-GTP |
| 5:1 | 7 | |

EXAMPLE 4

In Vivo Assays: The Results of the In Vivo Experiments are Provided in Tables IV and V Hereinbelow

TABLE IV

| | $IC_{50}$ Value (mM) | | | | | |
|---|---|---|---|---|---|---|
| | Flu A/NWS | Tox | HRV 14 | Tox | CVB3 | Tox |
| 3'-dA | 0.8 | 1.4 | 0.048 | 0.13 | ND | ND |
| 3'-dC | 0.9 | 5 | 0.025 | 1.8 | 0.09 | 1.8 |
| 3'-dG | 0.27 | 2.1 | 0.28 | 3.4 | ND | ND |
| 3'-dU | 0.085 | 12.5 | 0.027 | 2.4 | 0.09 | 2.4 |
| 3'-OMeA | NA | >50 | NA | >50 | ND | ND |
| 3'-OMeC | NA | >50 | NA | >50 | ND | ND |
| 3'-OMeG | NA | >50 | NA | >50 | ND | ND |
| 3'-OMeU | NA | >50 | NA | >50 | ND | ND |
| 3'-AzdU | NA | >12.5 | ND | ND | NA | >12.5 |
| 3'-AzdC | NA | >12.5 | ND | ND | NA | >12.5 |

TABLE V

MOUSE MODEL

| Dose (mg/kg) | MST (Days) | % ILS* | % Survival (14 Days) |
|---|---|---|---|
| Control | 10 | | 0 |
| 3'dC 200 mg/kg | 11 | 10 | 0 |
| 600 mg/kg | 12 | 20 | 10 |
| 3'dU 200 mg/kg | >14 | >40 | 60 |
| 600 mg/kg | 10 | 0 | 10 |

Note: 5 mice were used in each experimental group
*% ILS-increase in life span

As can be seen by the results provided hereinabove, several 3'-deoxy and 3'-substituted ribonucleosides are examined for antiviral activity and cytotoxicity in cell culture and as inhibitors of viral RNA polymerases in vitro. The rationale for conducting these studies is that 3'-modified nucleosides are known to act as chain terminators and inhibit the elongation of polynucleotides; however, most of the work to date has been directed toward inhibition of DNA synthesis by use of 2'-deoxy analogues which have been further modified at the 3' position. By retaining the 2'-hydroxyl group, these 3'-modified analogues have specificity for RNA synthesis. Depending on the binding affinities of these analogues for viral RNA polymerases relative to cellular RNA polymerases, specific inhibitors of viral replication exist.

3'-dCTP, 3'-dUTP and 3'-dGTP are effective inhibitors of transcription with the RNA-dependent RNA polymerase of poliovirus (a picornavirus). All three inhibit transcription very similarly except that 3'dATP is a less active inhibitor at a molar ratio 1:1 with the low molecular weight template.

The degree of inhibition dramatically depends on the molecular weight of the RNA-template. Such dependence is explained only if the analogues work as terminators of growing RNA chains. This experimental result is in agreement with theoretical considerations of the probability of incorporation of the terminators into synthesized RNA.

A correct comparison of efficiency of the analogues as inhibitors can be done for different RNA-polymerases if templates with similar molecular weight are used. This conclusion must also be taken into account when results of experiments in vivo are considered.

3'-deoxy-UTP is moderately active against the influenza virus RNA polymerase and has little or no effect on VSV RNA polymerase. 3'-deoxy-CTP has low to moderately inhibitory activity against influenza RNA polymerase, It does not inhibit VSV RNA polymerase. 3'-deoxy-GTP is a fairly good inhibitor of influenza virus RNA polymerase but is only weakly inhibitory towards the VSV polymerase.

None of the analogues tested have any significant activity against the DNA viruses Herpes Simplex types 1 and 2. On the other hand, the 3'-deoxyribonucleosides exhibit some activity against all of the RNA viruses tested in tissue culture. While the activity against influenza A virus is modest, much more potent antiviral activity is seen with members of the picornavirus group (HRV 14 and $CVB_3$). Of the analogues tested, 3'-dU has the best activity. Substitutions on the 3'-dU (3'-azido or 3'methyl ester) result in no antiviral activity.

There are no suitable animal models of HRV or CVB infection in which to assess the antiviral activity of these compounds. Therefore the compounds are only tested against a murine model of influenza A virus infection. In this model, 3'-deoxyribocystosine has minimal antiviral activity at the doses tested but 3'-dU shows significant protection of animals at a dose of 200 mg/kg given daily, as evidenced by the increase in life span of treated animals. The drug 3'-deoxyribouracil (3'0dU) appears to have toxicity at the higher dose level.

These data indicate that the results from the in vitro and in vivo studies are for the most part compatible-compounds that are potent inhibitors of picornaviral (poliovirus) RNA transcription in vitro are effective inhibitors of picornaviral replication in vivo, and compounds that are weak to moderate inhibitors of influenza viral RNA transcription in vitro are likewise moderately effective against viral replication in vivo.

BIBLIOGRAPHY

1. Walker, R. T., De Clercq, E., Eckstein, F. Nucleoside Analogue; Chemistry, Bilogy and Medical Application. Eds.; Nato Advances Study Institutes Series: Serie A, Life Sciences Vol. 26; Plenum Press: New York, 1979.

2. Gosselin, G., Bergogne, M-C. Rudder, J., Clercq, E., Imbach, J-L. Systematic Synthesis and Biological Evaluation of α- and β-D-Xylofuranosyl Nucleosides of the five naturally occurring bases in nucleic acids and related analogues. J. Med. Chem. 1986,29,203–214.

3. Axelrod, V. D., Vartikyan, R. M., Aivazashvilli, V. A., Bebelashvilly, R. S. Specific termination of RNA polymerase synthesis as a method of RNA and DNA sequencing. Nucleic Acids Res. 1978,5, 549–3553.

4. Axelrod, V. D., Kramer, F. R. Transcription from bacteriophage T7 and SP6 RNA polymerase promoters in the presence of 3'-deoxyribonucleoside 5'-triphosphate chain terminators. Biochemistry, 1985,24,5716–5723.

5. Kramer, F. R., and Mills, D. R. RNA sequencing with radioactive chain-terminating ribonucleotides. Proc. Natl. Acad. Sci. U.S.A., 1978,75,5334–5338.

6. Kutateladse, T. V., Bebelashvill, R. Sh., Alexandrova, L. A., Obukhov, A. G., Kraevsky, A. A. Analogs of nucleoside triphosphates with modified sugar residues as substrates for RNA polymerase. Molekularnaya Biologia, 1986,20, 267–276.

7. Goswami, B B. and Sharma, S. K. Inhibition of vaccinia virus growth and virus-specific RNA synthesis by 3'-O-methyl adenosine and 3'-O-methyl guanosine. J. Virology. 1983,45,1164–1167.

8. Puech, F., Gosselin, G., Imbach, J-L. Synthesis of 9-(3-Deoxy-3-fluor-D-ribofuranosyl)guanine, a new potent antiviral agent. J. Chem. Socl, chem. Commun., 1989, 955–957.

9. Plotch, S. J. Palant, O., and Gluzman, Y. Purification and propterties of poliovirus RNA polymerase expressed in *Escherichia coli.* J. Virology, 1989, 63,216–225.

10. Plotch, S. J. and Krug, R. M. Influenza virion transcriptase: Synthesis in vitro of large, polyadenylic acid-containing complementary RNA. J. Virology, 1977,21, 24–24.

11. Plotch, S. J., Tomasz, J., and Krug, R. M. Absence of detectable capping and methylating enzymes in influenza virions. J. Virology, 1978,28,75–83.

12. Beckes, J. D., Haller, A. A., and Perrault, J. Differential effect of ATP concentration on synthesis of vesicular stomatitus virus leader RNAs and mRNAs. J. Virology, 1987,61,3470–3478.

13. Tuschall, M., Hiebert, E., and Flanegan, J. B. Poliovirus RNA-dependent RNA polymerase synthesizes full-length copies of poliovirion RNA, cellular mRNA, and several plant virus RNAs in vitro. J. Virology. 1982,44, 209–216.

What is claimed is:

1. A method for controlling or treating RNA viral infections and not DNA viral infections in plants or animals, said method comprising: administering to said plants or animals an RNA-terminating amount of 3'-deoxyribocytosine, 3'-deoxyribouracil, 3'-deoxyriboguanine or combinations thereof.

2. A method according to claim 1, wherein said animals are avian, fish or mammals.

3. A method according to claim 2, wherein said RNA viral infections are picornaviruses.

4. A method according to claim 1, wherein said RNA viral infection is in plants.

5. A method according to claim 4, wherein said RNA viral infections are comoviruses.

6. A method according to claim 2, wherein said RNA-chain-terminating amount is 0.01 to 10,000 mg/kg.

7. A method according to claim 3, wherein said RNA-chain-terminating amount is 0.01 to 10,000 mg/kg.

8. A method according to claim 4, wherein said RNA-chain-terminating amount is 0.001 mM to 100 mM.

9. A method according to claim 5, wherein said RNA-chain-terminating amount is 0.01 mM to 10,000 mM.

* * * * *